United States Patent [19]

Collins

[11] 4,024,862

[45] May 24, 1977

[54] DRAPE FOR EXPANDED SURGICAL PROCEDURE

[75] Inventor: Robert F. Collins, Barrington, Ill.

[73] Assignee: The Kendall Company, Boston, Mass.

[22] Filed: May 12, 1976

[21] Appl. No.: 685,573

[52] U.S. Cl. .............................................. 128/132 D
[51] Int. Cl.² ................... A61F 13/00; A61L 15/00
[58] Field of Search ............. 128/132, 171, 132 D; 119/23

[56] References Cited

UNITED STATES PATENTS

| 388,385 | 8/1888 | Wooster | 119/23 |
|---|---|---|---|
| 3,244,148 | 4/1966 | Long | 119/23 |
| 3,667,458 | 6/1972 | Krebs | 128/132 D |
| 3,799,161 | 12/1973 | Collins | 128/132 D |
| 3,882,859 | 5/1975 | Erickson | 128/132 D |

*Primary Examiner*—Aldrich F. Medbery
*Attorney, Agent, or Firm*—Powell L. Sprunger

[57] ABSTRACT

A sterile drape for selectively performing an expanded surgical procedure comprising, a flexible main sheet having a lower surface facing toward a patient after placement of the drape, and an upper surface facing away from the patient after placement of the drape. The drape has a fenestration of a sufficient size for performing an enlarged surgical procedure. The drape also has a flexible frame sheet removably secured to the upper surface of the drape around the fenestration. The frame sheet has a fenestration of a size smaller than and aligned with the drape fenestration for performing a reduced surgical procedure. The frame sheet is removed from the drape for performing the enlarged surgical procedure through the drape fenestration.

14 Claims, 11 Drawing Figures

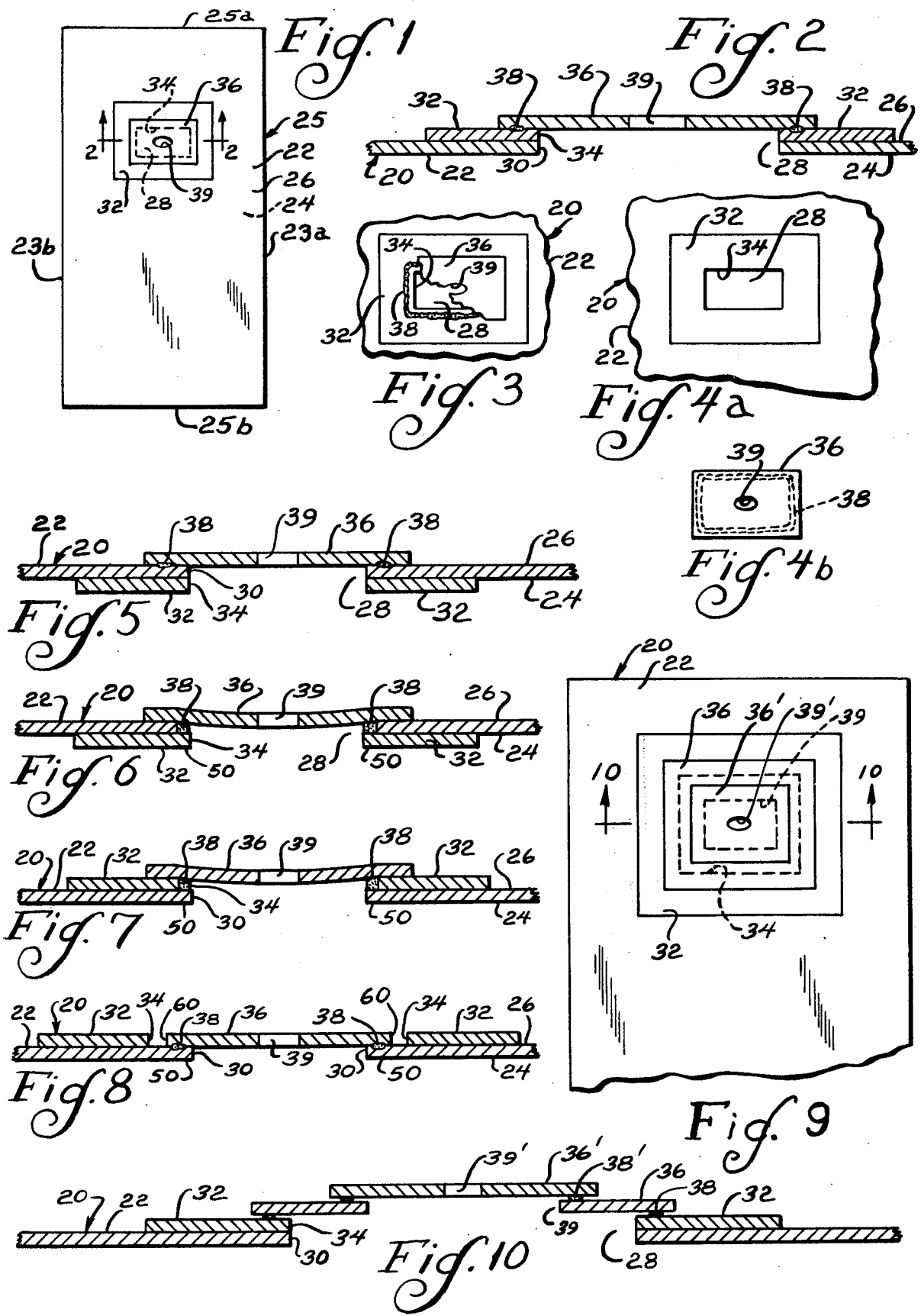

DRAPE FOR EXPANDED SURGICAL PROCEDURE

BACKGROUND OF THE INVENTION

The present invention relates to drapes, and more particularly to surgical drapes.

A various assortment of drapes have been proposed for surgical procedures, during which the drapes are used to cover the body of a patient and maintain a sterile barrier around the operative site while the procedure is performed through a fenestration in the drape. In the past, such drapes have been provided with fenestrations of a predetermined size for use in a particular surgical procedure depending upon the size and location of the surgical site. Accordingly, an excessive number of drapes have been required, and drapes must sometimes be replaced or cut pursuant to related procedures. For example, a drape having a relatively small fenestration is normally utilized for performing a breast biopsy, but, depending upon the results from pathology, it may be necessary to use a different drape having a larger fenestration for radical mastectomy. Similarly different drapes have been required for laparotomy procedures on children and adults, and it has thus been necessary for hospitals to maintain a stock of different drapes for performing the different procedures. Alternatively, the fenestration of a drape designed for a smaller surgical procedure must be cut to enlarge the fenestration for an expanded surgical procedure, which has been time consuming and inconvenient for the operating room team, as well as increasing the likelihood of contamination of the drape.

SUMMARY OF THE INVENTION

A principal feature of the present invention is the provision of a drape for performing different surgical procedures which require operative sites of differing sizes.

The drape of the present invention comprises, a flexible main sheet having a lower surface facing toward a patient after placement of the drape, and an upper surface facing away from the patient after placement of the drape. The drape has a fenestration of a sufficient size for performing an enlarged surgical procedure. The drape also has a flexible frame sheet removably secured to the upper surface of the drape around the fenestration, with the frame sheet having a fenestration of a size smaller than and aligned with the drape fenestration.

A feature of the present invention is that a reduced surgical procedure requiring a relatively small operative site may be performed through the fenestration of the frame sheet.

Another feature of the invention is that the frame sheet may be readily removed from the drape to expose the drape fenestration for performing an expanded surgical procedure requiring a relatively large operative site.

Thus, a feature of the present invention is that the drape may be used in a simplified and convenient manner to perform separate surgical procedures requiring fenestrations of different sizes.

Still another feature of the invention is that the drape may have a plurality of frame sheets having fenestrations of differing sizes for selectively performing a number of surgical procedures.

Further features will become more fully apparent in the following description of the embodiments of this invention and from the appended claims.

DESCRIPTION OF THE DRAWINGS

In the drawings:

FIG. 1 is a top plan view of a surgical drape of the present invention;

FIG. 2 is a fragmentary sectional view taken substantially as indicated along the line 2—2 of FIG. 1;

FIG. 3 is a fragmentary top plan view, partly broken away, of the drape of FIG. 1;

FIG. 4a is a fragmentary top plan view of the drape of FIG. 1 after removal of a frame sheet from the drape;

FIG. 4b is a top plan view of the frame sheet for the drape of FIG. 1;

FIG. 5 is a fragmentary sectional view of another embodiment of the drape of the present invention.

FIG. 6 is a fragmentary sectional view of another embodiment of the drape of the present invention;

FIG. 7 is a fragmentary sectional view of another embodiment of the drape of the present invention;

FIG. 8 is a fragmentary sectional view of another embodiment of the drape of the present invention;

FIG. 9 is a fragmentary top plan view of another embodiment of the drape of the present invention; and FIG. 10 is a fragmentary sectional view taken substantially as indicated along the line 10 —10 of FIG. 9.

DESCRIPTION OF THE PREFERRED EMBODIMENTS

Referring now to FIGS. 1–3, there is shown a surgical drape designated generally 20 having a flexible main sheet 22 which is preferably of a sufficient size to substantially cover the body of a patient. The main sheet 22 has a pair of side edges 23a and 23b, a pair of end edges 25a and 25b connecting the side edges 23a and b, a lower surface 24 facing toward the patient after placement of the drape, and an upper surface 26 facing away from the patient's body after placement of the drape. The main sheet 22 may be made from any suitable material, such as cotton, nonwoven fabric, or plastic.

The main sheet 22 has a fenestration 28 defined by peripheral edges 30 in the sheet which are of a sufficient size for performing an enlarged or expanded surgical procedure requiring a relatively large operative site. For example, the fenestration 28 of the drape 20 may be appropriately sized and located for performing radical mastectomy or a laparotomy procedure on an adult. However, it will be understood that the drape fenestration 28 may be appropriately located and sized for other surgical procedures, as desired.

Preferably, the drape has a reinforcement strip 32 secured to the upper surface 26 of the main sheet 22 and extending peripherally around the fenestration 28, as shown. The reinforcement strip 32 may be made from any suitable material, such as plastic or a laminate of nonwoven fabric and polyethylene, and the reinforcement strip is secured to the main sheet 22 by suitable means, such as heat sealing, adhesive, or crimping. The reinforcement strip 32 has peripheral edges 34 which extend around the fenestration 28, and, in this embodiment of the invention, the peripheral edges of the reinforcement strip are coextensive with the peripheral edges of the main sheet 22. The reinforcement strip serves to strengthen the sheet 22 in the region around the fenestration 28, and provide a fluid impervious barrier to prevent passage of liquid through the drape 20 while performing a surgical procedure.

The drape 20 also has a frame sheet 36 which is removably secured to the upper surface of the drape over the fenestration 28, with the frame sheet 36 being sufficiently large to extend across the drape fenestration. The frame sheet may be made of any suitable material such as a nonwoven fabric, polyethylene, or a laminate of polyethylene and nonwoven fabric. In a preferred form, the frame sheet includes a plastic material facing toward the fenestration 28 of the drape 20, in order to provide a fluid impervious barrier over the fenestration 28. The frame sheet 36 is removably secured to the upper surface of the reinforcement strip by suitable means, such as a line of adhesive 38 extending peripheraly around the fenestration 28. However, it is contemplated that the reinforcement strip may be omitted from the drape, and the frame sheet may be removably secured to the main sheet without the reinforcement strip.

As shown, the frame sheet 36 has a fenestration 39 aligned with the fenestration 28 of the drape 20. The fenestration 39 of the frame sheet 36 has a size smaller than the size of the drape fenestration 28, in order to perform a reduced surgical procedure requiring a relatively small surgical state.

In use, the drape 20 is positioned over the body of the patient, and the reduced surgical procedure, such as breast biopsy, is performed through the fenestration 39 of the frame sheet 36. In the event that the results from pathology indicate that a radical mastectomy will be required, the frame sheet 36 may be removed from the drape, as shown in FIG. 4a, in order to expose the enlarged fenestration 28 of the drape 20 through which the expanded surgical procedure, in this case radical mastectomy, is performed. Thus, the drape of the present invention permits performance of more than one surgical procedure at a single location on the patient, and eliminates the necessity of removing and replacing drapes, or enlarging a fenestration by cutting. Other suitable uses for the drape of the present invention include separate laparotomy procedures for a child and adult, in which the laparotomy procedure for the child is performed through the smaller fenestration 39 of the frame sheet 36, and the frame sheet 36 may be removed from the drape for performing the laporatomy procedure on the adult through the enlarged fenestration 28 of the drape. In a preferred form, the reinforcement strip 32 includes a plastic material facing toward the frame sheet 36, with release characteristics between the adhesive and plastic being such the adhesive 38 remains on the frame sheet 36, as shown in FIGS. 4a and 4b, when the frame sheet 36 is removed from the drape 20.

Another embodiment of the present invention is illustrated in FIG. 5, in which like reference numerals designate like parts. In this embodiment, the reinforcement strip 32 is secured to the lower surface 24 of the mains sheet 22 of the drape 20, with the peripheral edges 34 and 30 of the reinforcement strip and main sheet, respectively, being coextensive, as previously described. The frame sheet 36 is removably secured by adhesive 38 to the upper surface 26 of the main sheet 22 over the fenestration 28.

Another embodiment of the present invention is illustrated in FIG. 6, in which the reinforcement strip 32 is secured to the lower surface 24 of the main sheet 22 of the drape 20. However, in this embodiment, the peripheral edges 30 of the main sheet 22 are set back from the peripheral edges 34 of the reinforcement strip 32 in order to define marginal edges 50 of the reinforcement strip 32 which extend peripherally around the fenestration 28. The frame sheet 36 is removably secured to the marginal edges 50 of the reinforcement strip by adhesive 38 extending peripherally around the fenestration 28.

Another embodiment of the present invention is illustrated in FIG. 7, in which the reinforcement strip 32 is secured to the upper surface 26 of the main sheet 22 of the drape 20. In this embodiment, the peripheral edges 34 of the reinforcement strip 32 are set back from the peripheral edges 30 of the main sheet 22 in order to define marginal edges 50 of the main sheet 22 extending around the fenestration 28. The frame sheet 36 is removably secured to the marginal edges 50 of the main sheet peripherally around the fenestration 28 by adhesive 38.

Another embodiment of the present invention is illustrated in FIG. 8, in which like reference numerals designate like parts. The reinforcement strip 32 is secured to the upper surface 26 of the main sheet 22, and the frame sheet 36 is removably secured to the marginal edges 50 of the main sheet, as previously descried. However, in this embodiment, the peripheral edges 34 of the reinforcement strip 32 are set back a sufficient distance from the peripheral edges 30 of the main sheet 22, such that the peripheral edges 34 extend around peripheral edges 60 of the frame sheet 36.

Another embodiment of the drape of the present invention is illustrated in FIGS. 9 and 10, in which like reference numerals designate like parts. In this embodiment, the drape 20 has a first frame sheet 36 releasably secured by adhesive 38 to the upper surface of the drape 20 around the fenestration 28. The first frame sheet 36 has a fenestration 39 of a size smaller than the fenestration 28 of the drape 20, and which is aligned with the fenestration 28. The drape also has a second frame sheet 36' which is releasably secured by adhesive 38' to an upper surface of the first frame sheet 36 around the fenestration 39. The second frame sheet 36' also has a fenestration 39' of a size smaller than the fenestration 39 of the first frame sheet 36, with the fenestrations 39 and 39' being aligned.

In use, one or both of the frame sheets 36' or 36 may be removed from the drape in order to define different sized fenestrations for separate surgical procedures. Thus, for a surgical procedure requiring a relatively small operative site, the surgical procedure may be performed through the fenestration 39' of the second frame sheet 36'. If a moderate sized fenestration is needed for the surgical procedure, the second frame sheet 36' may be removed from the first frame sheet 36 in order to expose the fenestration 39 of the first frame sheet 36 through which the surgical procedure is performed. In the event that a relatively large fenestration is required for the operation, the first frame sheet 36 is also removed from the drape in order to expose the drape fenestration 28 through which the expanded surgical procedure may be performed. Of course, any number of frame sheets having fenestrations of varying sizes may be overlapped in a manner as described in connection with the drape of FIGS. 9 and 10.

The foregoing detailed description is given for clearness of understanding only, and no unnecessary limitations should be understood therefrom, as modifications will be obvious to those skilled in the art.

I claim:

1. A sterile drape for selectively performing an expanded surgical procedure, comprising:
   a flexible main sheet having a lower surface facing toward a patient after placement of the drape, and an upper surface facing away from the patient after placement of the drape, said drape having a fenestration of a sufficient size for performing an enlarged surgical procedure; and
   a flexible frame sheet having a size greater than said drape fenestration and removably secured to the upper surface of the drape around said fenestration, said frame sheet having a fenestration of a size smaller than and aligned with the drape fenestration for performing a reduced surgical procedure, said frame sheet being removed from the drape for performing the enlarged surgical procedure though the drape fenestration.

2. The drape of claim 1 wherein said frame sheet is releasably adhered to the drape.

3. The drape of claim 2 wherein the drape includes a plastic material extending around the fenestration and facing toward the frame sheet, and in which the frame sheet is releasably adhered to said plastic material.

4. The drape of claim 1 wherein the frame sheet includes a plastic material facing toward the drape fenestration.

5. The drape of claim 1 including a flexible reinforcement strip secured to the main sheet and extending peripherally around the drape fenestration.

6. The drape of claim 5 wherin said reinforcement strip is secured to the upper surface of said main sheet.

7. The drape of claim 6 wherein said main sheet and reinforcement strip have coextensive peripheral edges extending around the drape fenestration.

8. The drape of claim 7 wherein said frame sheet is adhered to the reinforcement strip around the periphery of the drape fenestration.

9. The drape of claim 6 wherein said main sheet and reinforcement strip have peripheral edges extending around said drape fenestration, the peripheral edges of said reinforcement strip are set back from the periphral edges of the main sheet defining marginal edges of the main sheet extending peripherally around the drape fenestration, and in which said frame sheet is releasably adhered to the marginal edges of the main sheet peripherally around the drape fenestration.

10. The drape of claim 9 wherein the peripheral edges of the reinforcement strip are set back a sufficient distance from the peripheral edges of the main sheet for the peripheral edges of the reinforcement strip to extend around peripheral edges of the frame sheet.

11. The drape of claim 5 wherein said reinforcement strip is secured to the lower surface of said main sheet.

12. The drape of claim 11 wherein said main sheet and reinforcement strip have coextensive peripheral edges extending around the drape fenestration.

13. The drape of claim 11 wherein said main sheet and reinforcement strip have peripheral edges extending around said drape fenestration, the peripheral edges of the main sheet are set back from the peripheral edges of the reinforcement strip defining marginal edges of the reinforcement strip extending peripherally around the drape fenestration, and in which said frame sheet is releasably adhered to the marginal edges of the reinforcement strip peripherally around the drape fenestration.

14. The drape of claim 1 including a second frame sheet secured to an upper surface of the first frame sheet around the fenestration of the first frame sheet, said second frame sheet having a fenestration of a size smaller than and aligned with the fenestraton of the first frame sheet.

* * * * *